US011647895B2

(12) United States Patent
Polayes et al.

(10) Patent No.: US 11,647,895 B2
(45) Date of Patent: May 16, 2023

(54) PROTECTIVE COVER SET FOR A MEDICAL PROBE

(71) Applicant: Sheathing Technologies, Inc., Morgan Hill, CA (US)

(72) Inventors: Lawrence S. Polayes, Morgan Hill, CA (US); Jennifer Downing, San Jose, CA (US); Sengdara Srisavaththay, Hollister, CA (US); Richard James Stevens, San Jose, CA (US)

(73) Assignee: Sheathing Technologies, Inc., Morgan Hill, CA (US)

( * ) Notice: Subject to any disclaimer, the term of this patent is extended or adjusted under 35 U.S.C. 154(b) by 0 days.

(21) Appl. No.: 17/319,415

(22) Filed: May 13, 2021

(65) Prior Publication Data

US 2021/0393236 A1    Dec. 23, 2021

Related U.S. Application Data

(63) Continuation of application No. 16/226,538, filed on Dec. 19, 2018, now Pat. No. 11,033,178.

(51) Int. Cl.
*A61B 8/00* (2006.01)
*A61B 8/12* (2006.01)
*A61B 1/00* (2006.01)

(52) U.S. Cl.
CPC ............ *A61B 1/00142* (2013.01); *A61B 8/12* (2013.01); *A61B 8/4281* (2013.01); *A61B 8/4444* (2013.01); *A61B 8/4422* (2013.01)

(58) Field of Classification Search
CPC ..... A61B 1/00142; A61B 8/12; A61B 8/4281; A61B 8/4422; A61B 8/4444; B32B 1/02; B32B 1/08

See application file for complete search history.

(56) References Cited

U.S. PATENT DOCUMENTS 3,809,230 A * 5/1974 Poncy .................... G01K 13/25
                                                    493/189
5,069,337 A    12/1991 Bala
5,795,632 A *  8/1998 Buchalter ................ A61B 8/12
                                                    383/211

(Continued)

FOREIGN PATENT DOCUMENTS

CN          107624051 A      1/2018
WO     WO-2017070746 A1     5/2017
WO     WO-2020131419 A1     6/2020

OTHER PUBLICATIONS

"U.S. Appl. No. 16/226,538, Examiner Interview Summary dated Mar. 11, 2021", 3 pgs.
"U.S. Appl. No. 16/226,538, Non Final Office Action dated Dec. 15, 2020", 16 pgs.
"U.S. Appl. No. 16/226,538, Notice of Allowance dated Mar. 31, 2021", 8 pgs.
"U.S. Appl. No. 16/226,538, Response filed Mar. 12, 2021 to Non Final Office Action dated Dec. 15, 2020", 11 pgs.

(Continued)

*Primary Examiner* — Yan Lan
(74) *Attorney, Agent, or Firm* — Schwegman Lundberg & Woessner, P.A.

(57) ABSTRACT

A protective cover set for a medical probe that includes a joint that seals both a moisture resistant probe cover and a surrounding wrapper that provides a barrier against microbial intrusion into the space between the outer wrapper and the probe cover. The sealed joint fixes the probe cover in place in relation to the outer wrapper. In some examples, the sealed joint secures a prefabricated probe cover with a three-dimensional non-planar shape in relation to the outer wrapper.

8 Claims, 6 Drawing Sheets

(56) References Cited

U.S. PATENT DOCUMENTS

| | | |
|---|---|---|
| 5,910,113 A | 6/1999 | Pruter |
| 5,997,481 A | 12/1999 | Adams et al. |
| 6,039,694 A | 3/2000 | Larson et al. |
| 6,224,543 B1 | 5/2001 | Gammons et al. |
| 6,402,695 B1 | 6/2002 | Grimm |
| 7,357,788 B2 | 4/2008 | Gammons |
| 7,665,893 B2 | 2/2010 | Buchalter |
| 8,118,743 B2 | 2/2012 | Park et al. |
| 9,433,468 B2 | 9/2016 | Wilt et al. |
| 10,154,828 B2 | 12/2018 | Buchalter |
| 11,033,178 B2 | 6/2021 | Polayes et al. |
| 2005/0187520 A1* | 8/2005 | Gammons .......... A61B 1/00142 604/171 |
| 2006/0264751 A1 | 11/2006 | Wendelken et al. |
| 2008/0139944 A1 | 6/2008 | Weymer et al. |
| 2014/0259604 A1 | 9/2014 | Romano et al. |
| 2016/0135784 A1 | 5/2016 | Gharib |
| 2016/0278738 A1 | 9/2016 | Buchalter |
| 2016/0331344 A1 | 11/2016 | Hadzic |
| 2020/0196841 A1 | 6/2020 | Polayes et al. |

OTHER PUBLICATIONS

"U.S. Appl. No. 16/226,538, Response filed Nov. 13, 2020 to Restriction Requirement dated Oct. 26, 2020", 3 pgs.
"U.S. Appl. No. 16/226,538, Restriction Requirement dated Oct. 26, 2020", 6 pgs.
"DuPont™ Tyvek® for Medical and Pharmaceutical Packaging", DuPont, (Mar. 20, 2016), 39 pgs.
"International Application Serial No. PCT/US2019/064863, International Search Report dated Feb. 25, 2020", 2 pgs.
"International Application Serial No. PCT/US2019/064863, Written Opinion dated Feb. 25, 2020", 6 pgs.
"Preliminary Product Specifications and Miscellaneous Properties of DuPont™", Tyvek® 40L, (2017), 4 pgs.
Lauren, Renee Hernley, "An Ultrasound Probe Sheathing Device: Design, Development, and Evaluation", Thesis Master of Science in Mechanical Engineering at the Massachusetts Institute of Technology, (Jun. 2013), 92 pgs.
"International Application Serial No. PCT US2019 064863, International Preliminary Report on Patentability dated Jul. 1, 2021", 8 pages.

* cited by examiner

PROTECTIVE COVER SET FOR A MEDICAL PROBE

BACKGROUND

Many medical procedures involve inserting a probe, such as a transducer, a scope, or a camera, into a body cavity and positioning the device near a region of the body to be examined. Examples of such probes include ultrasound probes (also known as "transducers") and endoscopes. Given the high replacement costs of such medical devices, there is a need to protect them against contamination from bodily fluids so they can be reused. A variety of different protective probe covers have been developed to protect against biological contamination. While a probe cover can prevent contamination of a medical probe during a medical procedure, there remains the need to protect the probe cover against contamination before use. For this purpose, a variety of different outer wrappers (also referred to as "overwraps") have been designed. The outer wrappers typically consist of two rectangular plastic sheets that are joined together to form a pouch-like enclosure that maintains a dean environment for the probe cover before use.

SUMMARY

This specification describes embodiments of a protective cover set for a medical probe. Some embodiments of the protective cover set include a joint that seals both a moisture resistant probe cover and a surrounding wrapper that provides a barrier against microbial intrusion into the space between the outer wrapper and the probe cover. In some embodiments, the sealed joint fixes the probe cover in place in relation to the outer wrapper. In some of these embodiments, the sealed joint secures a prefabricated probe cover with a three-dimensional non-planar shape in relation to the outer wrapper.

In some embodiments, the sealed joint defines the profile of the probe cover or at least a portion of the profile of the probe cover.

Other embodiments include a peripheral sealed joint between the outer wrapper layers that circumscribes the primary sealed joint between the probe cover and the surrounding wrapper layers to provide an additional microbial barrier between the external environment and the domain between the probe cover and the outer wrapper.

In some embodiments, the outer wrapper is attached to the joint with a lower bonding strength than the probe cover, making it easy for the user to remove the outer wrapper without damaging or contaminating the probe cover.

The protective outer wrapper also can function as a storage and transport cover by protecting the probe cover against contamination by, for example, user contact prior to use with a medical probe.

The protective cover sets disclosed herein provide efficiencies in manufacture and in performance. For example, the use of a single bond or sealed joint to seal and/or secure the moisture resistant probe cover and the surrounding wrapper requires less labor than conventional approaches. In addition, the combined moisture resistance and anti-microbial properties of the probe cover and the outer wrapper enable filling the distal end of ultrasound probe cover with gel prior to packaging, without risk of package decomposition and microbial growth, and potential probe contamination.

In a preferred embodiment, a protective cover set for a medical probe includes a probe cover, an outer wrapper, and a bond of four or more layers. The probe cover includes a flexible thermoplastic polymer material and has a closed distal end and an open proximal end configured to receive a working end of a medical probe. The outer wrapper includes two protective layers on opposite sides of the probe cover. The bond of four or more layers includes two layers of the thermoplastic polymer material between the two protective layers, wherein the bond creates at least one sealed joint that encloses at least a portion of the probe cover between the protective layers.

In some embodiments, the probe cover includes two layers of the thermoplastic polymer material, and each of the protective layers includes a respective thermoplastic polymer material that is different from the thermoplastic polymer material of the probe cover layers.

In some examples, the bond of four or more layers adheres the two layers of the flexible thermoplastic polymer material of the probe cover to one another with a first bond strength, and the bond adheres a first one of the protective layers to an adjacent one of the two layers of the flexible thermoplastic polymer material of the probe cover with a second bond strength, where the first bond strength is at least twice as strong as the second bond strength. In some embodiments, the bond adheres a second one of the protective layers to an adjacent one of the two layers of the flexible thermoplastic polymer material of the probe cover with a third bond strength, where the first bond strength is at least twice as strong as the third bond strength In some embodiments, the bond defines a boundary of the closed distal end and two longitudinal sides of the probe cover. In some examples, the bond adheres two layers of the thermoplastic polymer material of the probe cover with a water impermeable seal along the boundary of the closed distal end and the two longitudinal sides of the probe cover. In some examples, the bond adheres the two protective layers along the boundary. In some embodiments, unconnected edge portions of the protective layers extend laterally outward beyond the boundary and are free to move independently of one another.

In some embodiments, the bond adheres a proximal end portion of the probe cover between proximal end portions of the protective layers. Some examples additionally include a second sealed joint between distal end portions of the protective layers that enclose an untethered distal portion of the probe cover. In some embodiments, the bond creates, on opposite longitudinal sides of the probe cover, a first sealed joint and a second sealed joint that enclose at least a proximal portion of the probe cover between proximal portions of the protective layers. In some embodiments, at least a distal end portion of the probe cover comprises a three-dimensional non-planar shape configured to receive the working end of a medical probe.

In some examples of the protective cover set, a distal portion of the probe cover is inverted within an interior portion of the probe cover and unattached to the interior portion of the probe cover.

Some embodiments of the protective cover set further include a second bond that physically connects a region of a first one of the two protective layers with an adjacent region of the probe cover to improve the ability to hold open the probe cover for probe insertion.)). Some examples additionally include a third bond that physically connects a region of a second one of the two protective layers with an adjacent region of the probe cover. In some embodiments, each of the second bond and the third bond adheres the two layers of the flexible thermoplastic polymer material of the probe cover to one another with a first bond strength, and the second bond adheres the first protective layer with the adjacent region of the probe cover with a second bond strength that is less than half the strength of the first bond strength. In some examples, the second bond adheres the first protective layer with the adjacent region of the probe cover with a second bond strength that is less than one-tenth the strength of the first bond strength. Some examples include one or more additional bonds that physically connect respective regions of the first one of the two protective layers with respective adjacent regions of the probe cover.

In some embodiments, the protective layers create a microbial barrier that inhibits microbial intrusion between the protective layers of the outer wrapper and the probe cover. Such a barrier may be used to maintain sterility of the cover, after a sterilization process.

In some embodiments, at least one of the protective layers includes a material selected from the group consisting of: plastic fibers; flash spun plastic fibers; paper; a plastic film; a multi-layer laminate; and a paper-plastic laminate.

In some embodiments, the protective layers are directly bonded together along a peripheral boundary that is spaced apart from and circumscribes the probe cover.

In some embodiments, a protective cover set for a medical probe includes a probe cover comprising two layers of a flexible thermoplastic polymer material, and an outer wrapper comprising a first protective layer and a second protective layer on opposite sides of the probe cover, wherein the first and second protective layers comprise respective material compositions that differ from the thermoplastic polymer material of the two probe cover layers. The two layers of the flexible thermoplastic polymer material of the probe cover are bonded to one another along a sealed joint with a first bond strength, and the first and second protective layers are bonded respectively to the adjacent ones of the two layers of the flexible thermoplastic polymer material of the probe cover along the sealed joint with second and third bond strengths respectively, wherein the first bond strength is at least twice as strong as the second and third bond strengths.

In some embodiments, a protective cover set for a medical probe includes a probe cover comprising a flexible thermoplastic polymer material having a three-dimensional non-planar shape configured to receive the working end of a medical probe, and an outer wrapper comprising outer protective layers on opposite sides of the probe cover. The two outer protective layers and the proximal end portion of the probe cover are bonded together along a common sealed joint that defines a profile of the proximal end portions of the probe cover, wherein a remaining portion of the probe cover beyond the bonded proximal end portion is unattached to the outer wrapper, and a remaining distal portion of the outer protective layers are bonded together along an extension of the sealed joint that is spaced apart from and encloses the remaining portion of the probe cover.

Other features, aspects, objects, and advantages of the subject matter described in this specification will become apparent from the description, the drawings, and the claims.

DETAILED DESCRIPTION

In the following description, like reference numbers are used to identify like elements. Furthermore, the drawings are intended to illustrate major features of exemplary embodiments in a diagrammatic manner. The drawings are not intended to depict every feature of actual embodiments nor relative dimensions of the depicted elements, and are not drawn to scale.

FIGS. 1A, 1B, 2A, and 2B show plan and cross-sectional end views of a protective cover set 10 for use with a medical probe, e.g., an ultrasound probe (not shown). The protective cover set 10 includes top and bottom sheets or layers 12, 14 of an outer wrapper 15. The top and bottom outer wrapper layers 12, 14 are disposed on opposite sides of a probe cover 16. The probe cover 16 has a closed distal end 18. The probe cover 16 also has an open proximal end 20 that is configured to receive a working end of an elongated medical probe. In some embodiments, the probe cover 16 is formed of two layers of a polymer. In other embodiments, the probe cover 16 is prefabricated with a three-dimensional non-planar shape that is designed to match or otherwise accommodate the exterior size and shape of an associated medical probe.

Figure 1A:
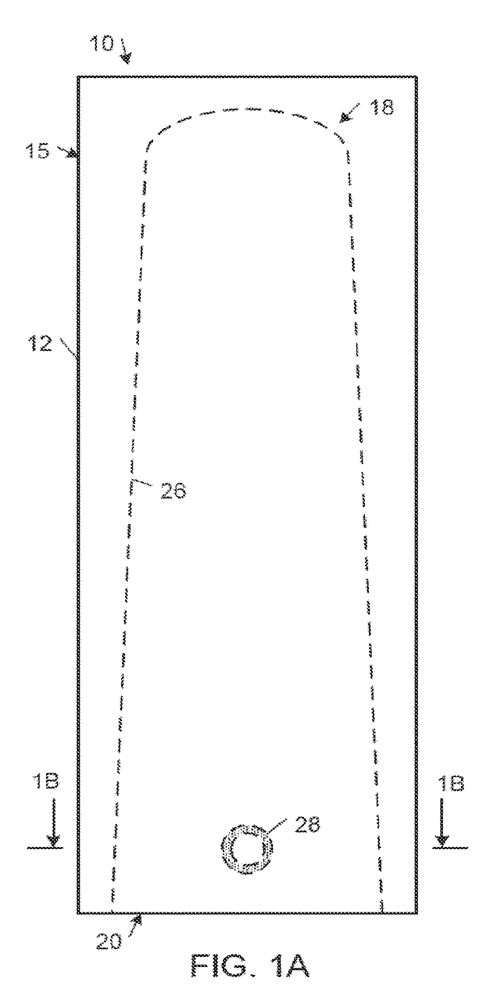
FIG. 1A is a plan view of a protective cover set ha includes a wrapper and a probe cover that are conjoined along a sealed joint.
Figure 1B:
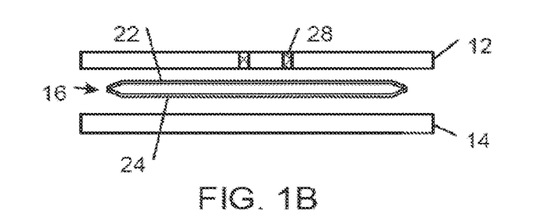
FIG. 1B is an exploded cross-sectional end view of an open proximal end of the protective cover set shown in FIG. 1A.

Referring to FIGS. 1A and 1B, in the illustrated embodiment, the probe cover 16 includes two layers 22, 24 of a flexible polymer. The two protective outer wrapper layers 12, 14 are disposed on opposite sides of the two flexible polymer layers 22, 24 of the probe cover 16. The protective outer wrapper layers 12, 14 and the flexible polymer layers 22, 24 are bonded together along a sealed joint 26 that defines a profile of the probe cover 16. In the embodiments disclosed herein, the protective outer wrapper layers 12, 14 and the flexible layers 22, 24 of the probe cover 16 may be joined together by a heat sealed bond.

Figure 2A:
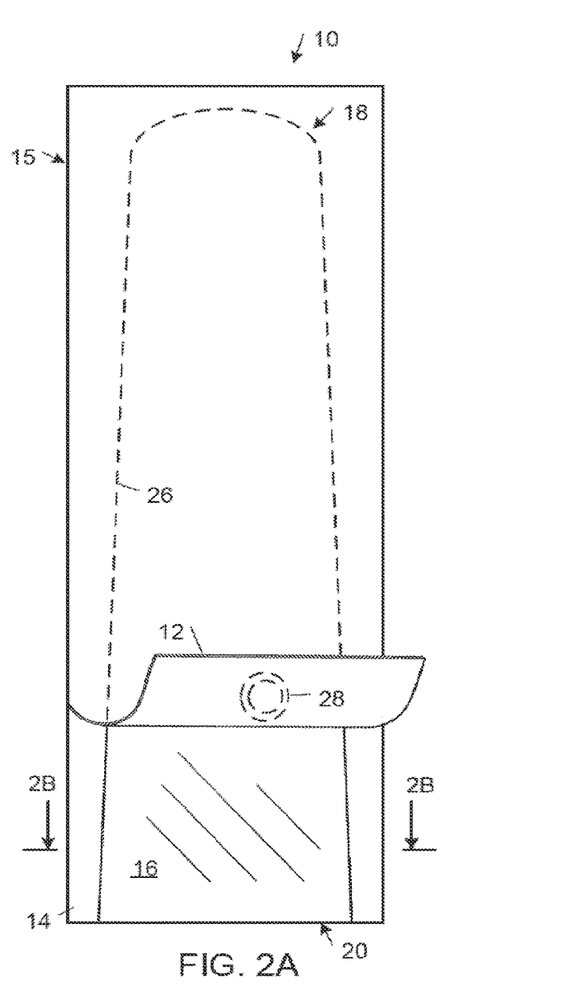
FIG. 2A is a top view of the protective cover set shown in FIG. 1A with a top portion of the wrapper peeled back from the proximal open end of the underlying probe cover.
Figure 2B:
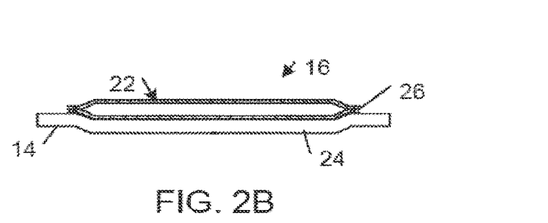
FIG. 2B is a cross-sectional end view of the proximal open end of the protective cover set shown in FIG. 2A.

Referring to FIGS. 2A and 2B, in the illustrated embodiment, the protective outer wrapper layers 12, 14 are attached to the sealed joint 26 with a lower bonding strength than the probe cover 16, making it easy for a user to remove the protective outer wrapper layers 12, 14 without damaging or contaminating the probe cover 16.

In some embodiments, at least one of the protective layers includes a material selected from the group consisting of: plastic fibers; flash spun plastic fibers; paper; a plastic film; a multi-layer laminate; and a paper-plastic laminate.

In some embodiments, the protective outer wrapper layers 12, 14 are formed of plastic fibers, such as flash spun plastic fibers, which may include one or more of flash spun polypropylene fibers, flash spun polyurethane fibers, flash spun nylon fibers, flash spun polyethylene fibers, and flash spun high density polyethylene (HDPE) fibers. In some of these embodiments, the plastic fibers are flash spun using heat and pressure. In some embodiments, the thickness of the outer wrapper layers 12, 14 is in the range of 2 mils to 10 mils (i.e., 0.05 mm to 0.25 mm). Utilizing wrapping layers formed from flash spun plastic fibers (e.g., high-density polyethylene (HDPE) fibers), not only protects the probe cover from physical damage but also provides an excellent microbial barrier that inhibits microbial intrusion into the domain between the protective outer wrapper 15 and the probe cover 16. In addition, biological contaminants generally cannot consume wrapper layers formed of plastic, nor do such wrapper layers promote the growth of biological contaminants.

In some embodiments, the probe cover is formed of flexible plastic film material, which may include one or more of polyethylene, polyurethane, polypropylene, and nylon.

In some embodiments, the outer wrapper layers 12, 14 and the probe cover 16 are formed from layers of different plastic compositions. For example, in an embodiment in which the outer wrapper layers 12, 14 are formed from polyethylene (e.g., HDPE), the probe cover 16 is formed from a polymer that is free of polyethylene, such as polyurethane, polypropylene, and nylon. In an embodiment in which the outer wrapper layers 12, 14 include polyurethane, the probe cover 16 is formed from a polymer that is free of polyurethane, such as polyethylene, polypropylene, and nylon. In an embodiment in which the outer wrapper layers 12, 14 include polypropylene, the probe cover 16 is formed from a polymer that is free of polypropylene, such as polyethylene, polyurethane, and nylon. In an embodiment in which the outer wrapper layers 12, 14 include nylon, the probe cover 16 is formed from a polymer that is free of nylon, such as polyethylene, polyurethane, and polypropylene. Other suitable combinations of non-similar or incompatible polymers may be readily determined by those of ordinary skill in the art The protective cover set 10 also includes a light thermal pressure bond 28 (also referred to herein as a "tack bond") that physically connects a region of a first one of the two outer wrapper layers 12, 14 with an adjacent region of the probe cover 16. In the illustrated embodiment, the tack bond 28 is between the proximal portion of the top outer wrapper layer 12 and the proximal portion of the underlying probe cover 16. In some embodiments, the tack bond 28 adheres the first outer wrapper layer (also referred to as the first "protective layer") with the adjacent region of the probe cover with a bond strength that is less than half the strength of the bond between the probe cover layers 12, 14. In some of these embodiments, the tack bond 28 adheres the first outer wrapper layer (also referred to as the first "protective layer") with the adjacent region of the probe cover with a bond strength that is less than one-tenth the strength of the bond between the probe cover layers 22, 24. The tack bond 28 enables the user to easily open the proximal end 20 of the probe cover 16 by manipulating the open proximal end 20 of the top outer wrapper layer 12.

In some embodiments, the protective cover set 10 includes multiple tack bonds. For example, in addition to the tack bond 28 that is formed between the top layer 12 of the outer wrapper 15 and the underlying probe cover layer 22, some embodiments additionally include a second tack bond between the bottom layer 14 of the outer wrapper 15 and the overlying probe cover layer 24 to further assist the user in manipulating the mouth portion of the probe cover to facilitate the insertion of a medical probe into the probe cover 16.

Figure 3A:
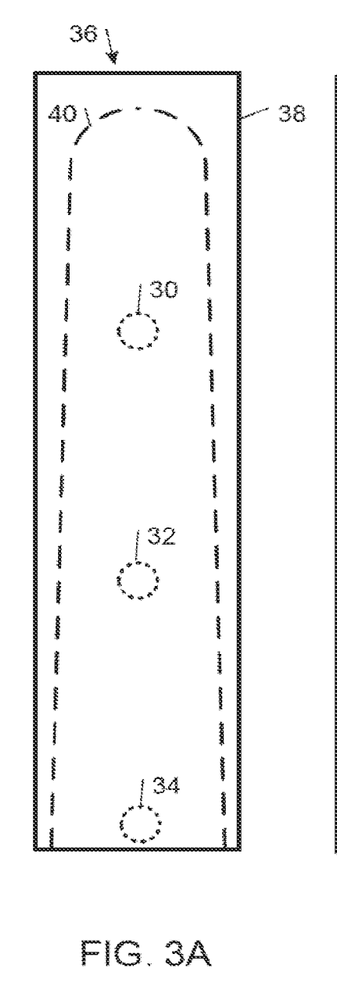
FIGS. 3A, 3B, and 3C each shows a top view of a respective cover set that includes a different respective set of longitudinally arranged bonds between an outer wrapper and a probe cover.
Figure 3B:
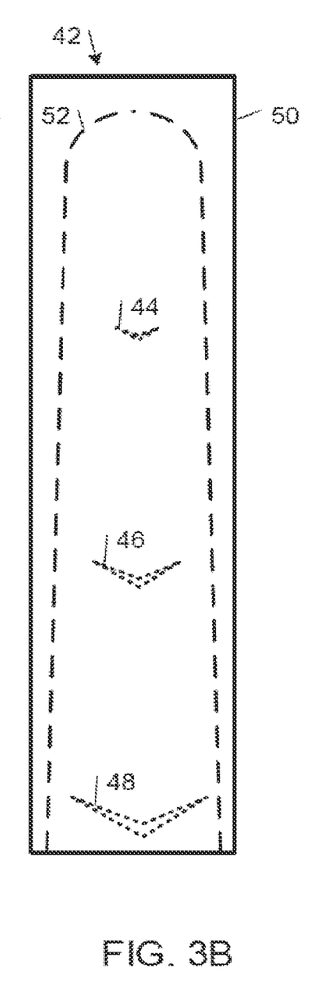
Figure 3C:
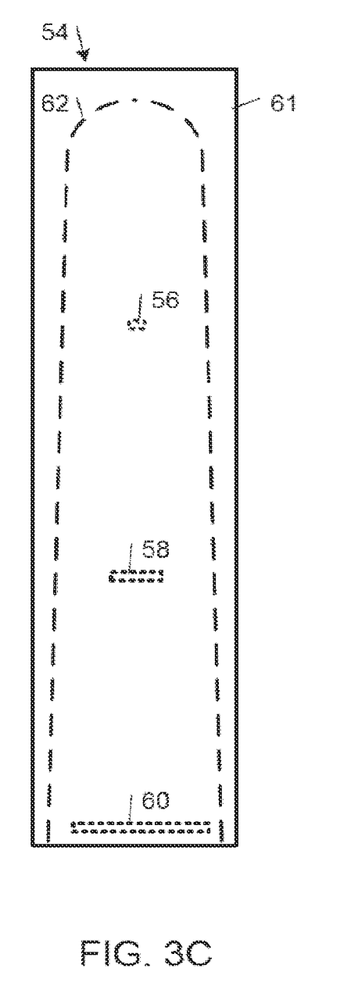

FIGS. 3A, 3B, and 3C show top views of cover sets that include different respective sets of longitudinally arranged tack bonds between protective outer wrappers and respective probe covers.

Referring to FIG. 3A, an example of a protective cover set 36 includes a set of three circular tack bonds 30, 32, 34 of the same size and distributed longitudinally along the length of the protective cover set 36. The tack bonds 30-34 adhere local regions of the interior surface of the outer wrapper 38 with the exterior surface of the probe cover 40 to facilitate opening the proximal end of the probe cover 40 and to maintain a smooth open interior shape along the length of the probe cover 40 while the user is inserting the distal end of a medical probe into the probe cover 40.

Referring to FIG. 3B, an example of a protective cover set 42 includes a set of three progressively smaller chevron-shaped tack bonds 44, 46, 48 that are distributed longitudinally from the proximal end to the distal end of the protective cover set 42. The tack bonds 44-48 adhere local regions of the interior surface of the outer wrapper 50 with local regions of the exterior surface of the probe cover 52 along the length of the probe cover 52 to facilitate opening the proximal end of the probe cover and maintaining a smooth open interior shape along the length of the probe cover 52 while the user is inserting the distal end of a medical probe into the probe cover 52. The center of each v-shaped chevron is closer to the proximal end of the protective cover set 42 than the peripheral ends of the chevron (i.e., each chevron is flared in the distal direction); this feature concentrates the force a user applies to the open proximal end of the protective cover set 42 along the longitudinal direction as the user is inserting the distal end of a medical probe into the probe cover. The sizes of the chevrons are progressively smaller from the proximal end to the distal end of the protective cover set 42 in order to reduce the force the user needs to apply to remove the wrapper layers 50 from the probe cover 52 while the user is inserting the distal end of a medical probe into the probe cover 52.

Referring to FIG. 3C, an example of a protective cover set 54 includes a set of three progressively smaller linear tack bonds 56, 58, 60 that are distributed longitudinally from the proximal end of the protective cover set 54 to the distal end of the protective cover set 54. The linear tack bonds 56, 58, 60 adhere the interior surface of the outer wrapper 61 with the exterior surface of the probe cover 62 to facilitate opening the proximal end of the probe cover and inserting the distal end of a medical probe. In particular, distributing the tack bonds 56-60 along the length of the protective cover set 54 maintains a smooth open shape along the length of the probe cover 62 when the user is inserting the distal end of a medical probe into the probe cover. In addition, progressively reducing the lengths of the tack bonds 56-60 from the proximal end to the distal end of the protective cover set 54 reduces the force the user needs to apply to remove the wrapper layers 61 from the probe cover 62 as the user is inserting a medical probe into the probe cover 62.

Each of the example protective cover sets 36, 42, and 54 described above in connection with FIGS. 3A, 3B, and 3C is merely exemplary and may be configured differently. For example, embodiments within the scope of the claims may include a variety of different configurations with greater or fewer features and the same or different feature sizes. For example, exemplary embodiments may include tack bonds of the same or different shapes and/or sizes that adhere the protective cover layers of the outer wrapper to adjacent local regions of the associated probe cover. The tack bonds may be arranged to adhere the first and second protective cover layers to first and second layers of the associated probe cover, respectively. Multiple tack bonds may be distributed between the protective layers of the outer wrapper and the probe cover, on one or both sides, and in any of a variety of different arrangements, including longitudinally, laterally, diagonally, randomly or, pseudo-randomly.

Figure 4A:
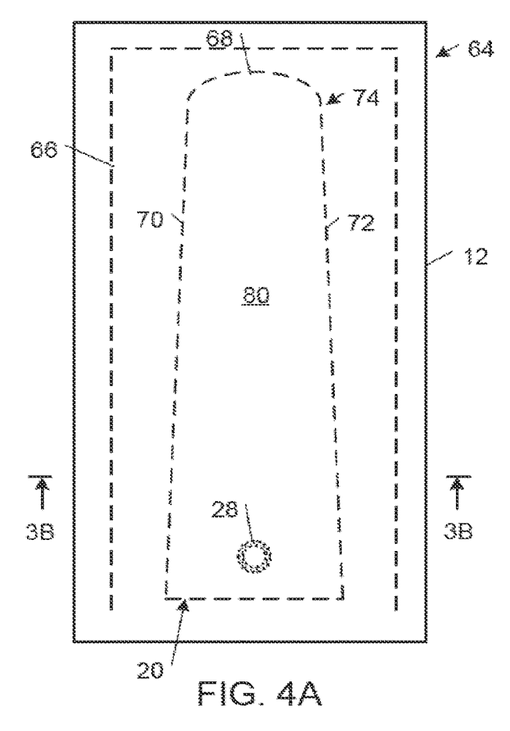
FIG. 4A is a plan view of a protective cover set that includes a wrapper and a probe cover that are conjoined along a primary sealed joint, and that further includes a peripheral sealed joint that circumscribes the side and distal lengths of the primary sealed joint.
Figure 4B:
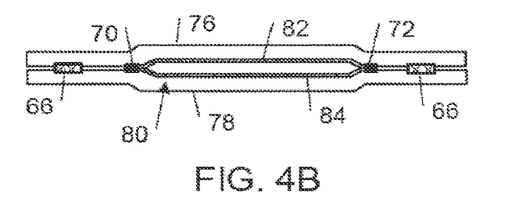
FIG. 4B is a cross-sectional end view of the protective cover set shown in FIG. 4A.

FIGS. 4A and 4B show an embodiment of a protective cover set 64 that includes a peripheral sealed joint 66 that circumscribes the distal end 68 and the side lengths 70, 72 of the primary sealed joint 74 that is formed between the outer wrapper layers 76, 78 and the probe cover 80. The peripheral sealed joint 66 bonds the outer wrapper layers 76, 78 directly to one another to provide a second microbial inhibiting barrier between the external environment and the four-layer bond that forms the primary sealed joint 74 between the probe cover layers 82, 84 and the microbe-inhibiting outer wrapper layers 76, 78.

Figure 5:
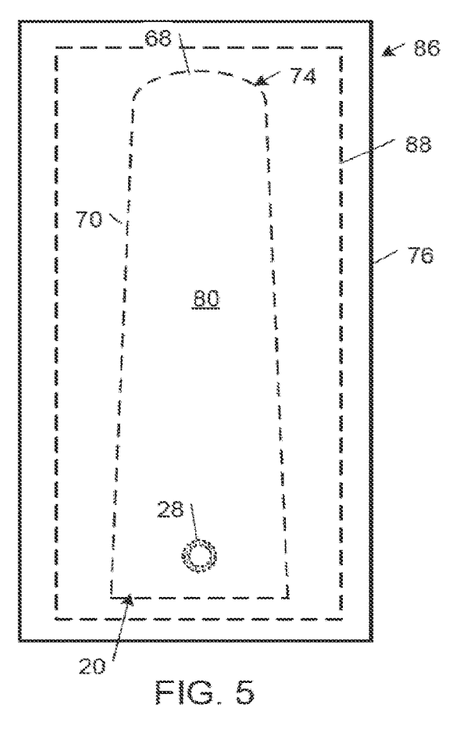
FIG. 5 is a plan view of a protective cover set that includes a wrapper and a probe cover that are conjoined along a primary sealed joint, and that further includes a peripheral sealed joint that completely circumscribes the primary sealed joint.

FIG. 5 shows a protective cover set embodiment 86 that includes a peripheral sealed joint 88 that completely circumscribes the four-layer bond that forms the primary sealed joint 74 between the outer wrapper layers 76, 78 and the layers 82, 84 of the probe cover 80. In this way, the peripheral sealed joint 74 and the peripheral sealed joint 88 jointly inhibit microbial intrusion into the space between the probe cover 80 and the outer wrapping layers 76, 78.

In some embodiments, the outer wrapper layers 12, 14 are bonded to each other along the peripheral sealed joint with a lower bonding strength than the bonding strength between the probe cover layers 22, 24, making it easy for the user to remove the outer wrapper while still providing a microbial barrier between the external environment and the probe cover 16. In some examples, the probe cover includes two layers of the thermoplastic polymer material, and each of the protective layers comprises a respective thermoplastic polymer material that is different from the thermoplastic polymer material of the probe cover layers. In some examples, the bond adheres the two layers of the flexible thermoplastic polymer material of the probe cover to one another with a first bond strength, and the bond adheres a first one of the protective layers to an adjacent one of the two layers of the flexible thermoplastic polymer material of the probe cover with a second bond strength, where the first bond strength is at least twice as strong as the second bond strength. In some of these examples, the bond adheres a second one of the protective layers to an adjacent one of the two layers of the flexible thermoplastic polymer material of the probe cover with a third bond strength, where the first bond strength is at least twice as strong as the third bond strength. In some examples, the first bond strength is at least five times as strong as the second bond strength and the third bond strength. In still other examples, the first bond strength is at least ten times as strong as the second bond strength and the third bond strength.

Figure 6:
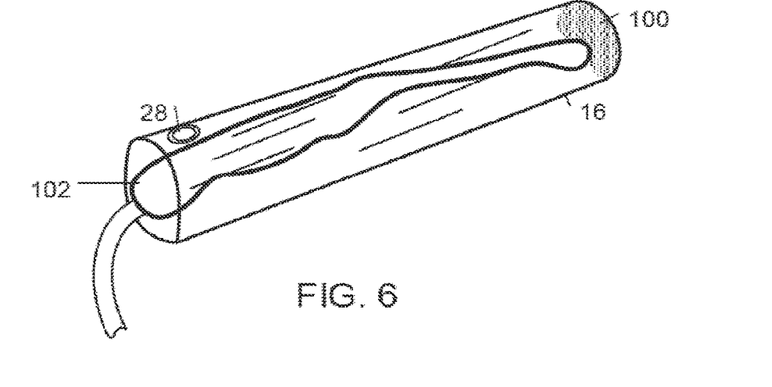
FIG. 6 is a perspective view of a medical probe inserted within a probe cover.

Referring to FIG. 6, in some embodiments, a gel 100 is placed inside in the distal end of the probe cover 16 prior to packaging. The gel 100 typically is loaded into the end of the probe cover after the sealed joint 26 is formed between the layers 12, 14, 22, 24 of the outer wrapper 15 and the probe cover 16. In some embodiments, the gel 100 may be, for example, an ultrasound transmission gel. Sealing the outer wrapper 15 with one or more sealed joints 26, as described above, provides an effective barrier against the intrusion of microbes into the domain of the probe cover 16, particularly when such sealed joints are formed of plastic materials which are resistive to microbial growth. In contrast, existing medical probe covers and protective cover sets do not provide an effective microbial barrier between the external environment and the probe cover 16. Additionally, many such protective cover sets have an outer layer made of paper or a paper laminate. Consequently, use of gels placed in such protective cover sets prior to packaging risk molding/spoilage of the outer wrapper, and concomitant contamination of the probe covers.

Placing the gel 100 in the distal end of the probe cover 16 prior to packaging, however, provides a significant convenience for the user (e.g., a medical practitioner) by obviating the extra time and effort that it would otherwise take to manually insert the gel 100 into the probe cover 16. In contrast, the protective cover sets described herein enable the user to start a medical examination without delay. In this process, the user picks up a protective cover set, such as the protective cover set 10 shown in FIGS. 1A-2B. The user manipulates the outer wrapper 15 and a proximal edge of the top wrapper layer 12 in the vicinity of the tack bond 28 to open the proximal end of the probe cover 16. The user inserts a medical probe into the probe cover 16. The user advances the distal end of the medical probe to the pre-gelled distal end of the probe cover 16. The user then lifts and removes the top layer 12 of the outer wrapper 15 to expose the top layer 22 of the probe cover 16. Next, the user removes the bottom layer 14 of the outer wrapper 15 to expose the entire probe cover 16. As shown in FIG. 6, the user can optionally manipulate the distal portion of the probe cover 16 to smooth the gel 100 over the tip of the medical probe 102 and remove any air bubbles. Thereafter, the user can use the medical probe 102 with the pre-gelled probe cover 16 to perform a medical examination.

In some pre-gelled protective cover set embodiments disclosed herein, the distal end of the protective cover set is folded to retain the pre-packaged gel 100 within the distal portion of the probe cover before use. In some embodiments, the protective cover set is stored within a secondary outer package is formed of a material (e.g., plastic coated aluminum foil or multilayer plastic) that has a very low moisture vapor transmission rate to protect the gel from drying out before use. In other embodiments, the outer two layers of the protective cover set are made from a material with a very low moisture vapor transmission rate. In some examples, the second outer packaging is designed to constrain movement of the pre-gelled protective cover set within the package and thereby maintain the fold in the distal portion of the probe cover. Some embodiments may include a spring clip or other retention mechanism to secure the fold at the distal end of the probe cover.

Some embodiments of the protective cover set embodiments that are disclosed herein include one or more adhesive closures, which may be implemented by adhesive tape closure strips or dispensed adhesive with an overlying liner. In some embodiments, one or more adhesive closures are provided on the inside surface at the proximal end of one or both of the top and bottom outer wrapper layers (e.g., layers 12 and 14 in the embodiment shown in FIG. 1A and 1B). The one or more adhesive closures may be used to secure one or both of the outer wrapper layers 12, 14 to a cable associated with a medical probe. In some embodiments, one or more adhesive closures are provided on the inside surface at the proximal end of one or both of the top and bottom probe cover layers (e.g., layers 22 and 24 in the embodiment shown in FIG. 1A and 1B). The one or more adhesive closures may be used to secure one or both of the probe cover layers 12, 14 to a medical probe.

Figure 7A:
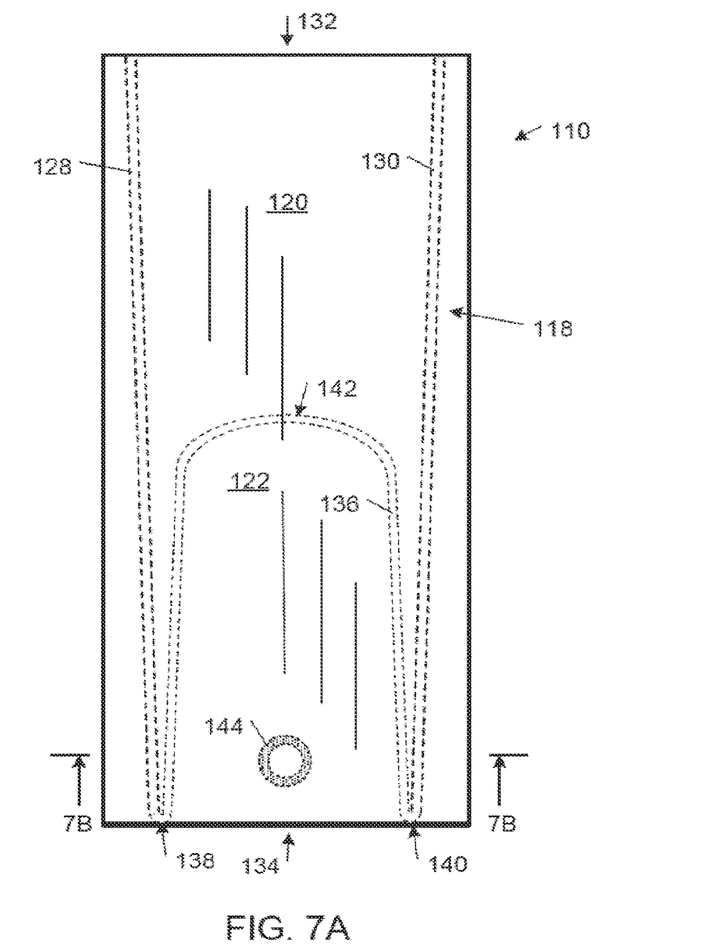
FIG. 7A is a plan view of a protective cover set that includes an outer wrapper and a probe cover that are conjoined along two sealed joints.
Figure 7B:
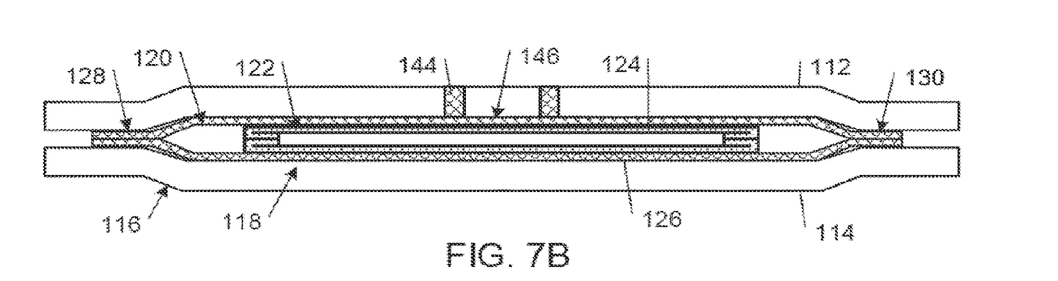
FIG. 7B is a cross-sectional end view of an open proximal end portion of the protective cover set shown in FIG. 7A.

FIGS. 7A and 7B show plan and cross-sectional end views of a protective cover set 110 for use with a probe, e.g., an ultrasound probe (not shown). The protective cover set 110 includes a top layer 112 and a bottom layer 114 of an outer wrapper 116 and an inner inverted probe cover 118 that includes a proximal section 120 and an inverted distal section 122. The top and bottom protective layers 112, 114 of the outer wrapper 116 are disposed on opposite sides of the probe cover 118. The probe cover 118 includes two layers 124, 126 of a flexible polymer. The protective layers 112, 114 and the portions of the flexible polymer layers 124, 126 in the proximal section 120 of the probe cover 118 are bonded together along two sealed joints 128, 130. The sealed joints 128, 130 define the profile of the proximal section 120 of the probe cover 118, which includes an open proximal end 132 and an open inverted end 134. The top and bottom probe cover layers 124, 126 also are joined together in the distal section 122 of the probe cover 118 along a distal sealed joint 136. In some embodiments, the distal sealed joint 136 is a continuous extension of the bonds between the flexible polymer layers 124, 126 in the proximal section 120 of the probe cover 118. The distal sealed joint 136 bonds the top and bottom probe cover layers 124, 126 to one another. In some embodiments, the inverted distal section 122 of the probe cover 118 is unattached to the outer wrapper 116 between the ends 138, 140 of the sealed joints 128, 130 and the distal end 142 of the probe cover 118.

The protective cover set 110 also includes a tack bond 144 between the distal portion of the top outer wrapper layer 112 and the distal portion of the proximal section 120 of the probe cover 118. The tack bond 144 adheres the top layer 112 of the outer wrapper 116 to a top surface 146 of the non-inverted probe cover layer 120. This feature enables the user to easily open the inverted portion 134 of the probe cover 118 simply by manipulating the outer wrapper 112 and the front edge of the opening 134. In some embodiments, the protective cover set 110 includes one or more other tack bonds.

Referring to FIGS. 8A, 8B, 9A, and 9B, there are shown plan and cross-sectional end views of a protective cover set 150 for use with a probe, e.g., an ultrasound probe (not shown). The protective cover set 150 includes top and bottom sheets or layers 152, 154 of an outer wrapper 155. In some embodiments, the outer wrapper sheets or layers 152, 154 are formed of a flash spun plastic fibers of the types described above in connection with the embodiments of FIGS. 1A-2B. The outer wrapper layers 152, 154 are disposed on opposite sides of an elongated probe cover 156. The probe cover 156 has a closed distal end 158 and an open proximal end 159 that is configured to receive a working end of an elongated medical probe. In some embodiments, the probe cover 156 is prefabricated with a three-dimensional non-planar shape that is designed to match or otherwise accommodate the external size and shape of an associated medical probe. As used herein, the term "prefabricated" means that the probe cover 156 is fabricated before it is joined to the outer wrapping layers 152, 154.

Figure 8A:
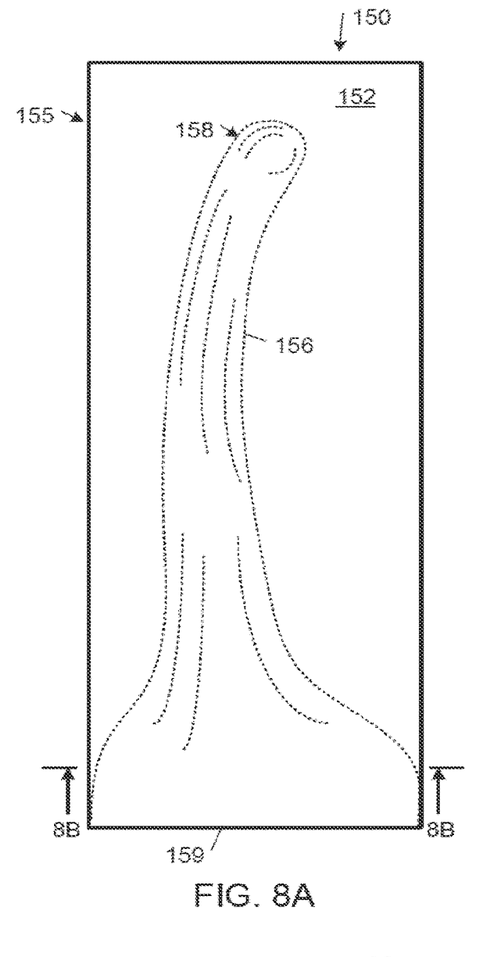
FIG. 8A is a plan view of a top protective layer overlying a three-dimensional non-planar probe cover.
Figure 8B:
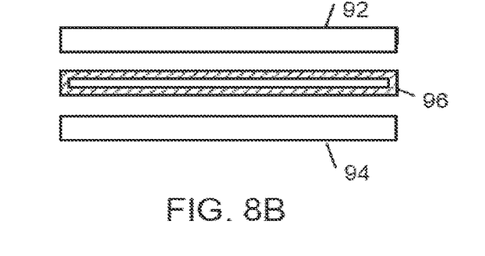
FIG. 8B is an exploded cross-sectional end view of a proximal open end portion of the protective layers and the probe cover shown in FIG. 8A.
Figure 9A:
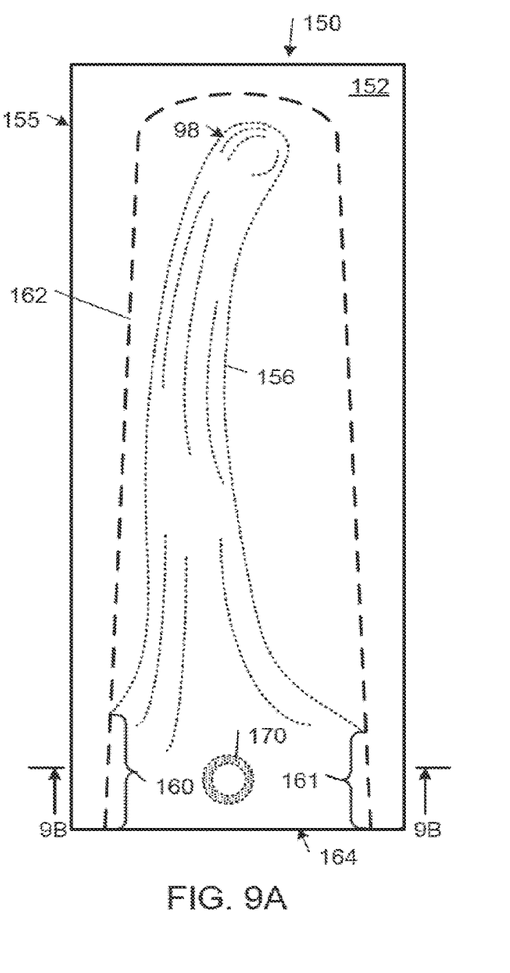
FIG. 9A is a plan view of a top protective layer overlying and bonded to the probe cover shown in FIG. 8A along a sealed joint along which flared portions of the proximal end of the probe cover are cropped.

In the illustrated embodiment, the prefabricated probe cover 156 has an elongated tubular shape with a closed distal end 158 and an open flared proximal end portion 160 and 161. The prefabricated probe cover 156 is sealed between the two protective outer wrapper layers 152, 154 by a sealed joint 162 that intersects the open flared proximal end portions 160, 161 of the probe cover 156 and circumscribes the profile of the remaining portions of the probe cover 156. Along the portions of the sealed joint 162 that do not intersect the probe cover 156, the sealed joint 162 directly bonds the outer wrapper layers 152, 154 to one another. Along the portions 160, 161 of the sealed joint 162 that intersect the open flared proximal end portion 159 of the probe cover 156, the sealed joint 162 bonds the outer wrapper layers 152, 154 with the layers in the flared portion 159 of the probe cover 156 that intersect the sealed joint 162. The sealed joint 162 fixes the probe cover 156 in place in relation to the outer wrapper 155. In some embodiments, the process of forming the sealed joint 162 crops the outer flared sides at the sealed joint 162, forming portions 160 and 161, as shown in FIG. 9A. This narrows the opening 164 at the proximal end 159 of the probe cover 156 and, thereby, improves the fit between the probe cover 156 and the medical probe.

Figure 9B:
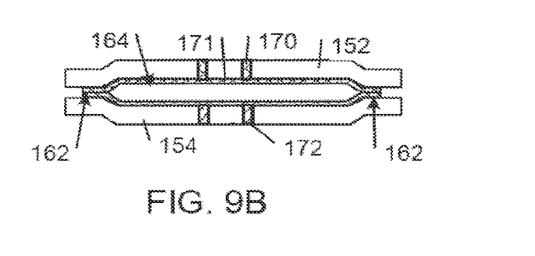
FIG. 9B is a cross-sectional end view of an open proximal end portion of the protective layer and the probe cover shown in FIG. 9A.

The protective cover set 150 also includes a tack bond 170 between the proximal portion of the top layer 152 of the outer wrapper 155 and the proximal portion of the probe cover 156. The tack bond 170 provides frictional or gripping features on the surface of the top layer 152 of the outer wrapper that are adhered to a top surface 171 at the proximal end 159 of the probe cover 156. This feature enables the user to easily open the proximal end 159 of the probe cover 96 simply by manipulating the outer wrapper 155 and the front edge of the proximal end 159 of the top layer 152 of the outer wrapper 155. In some embodiments, the protective cover set 150 includes a second tack bond 172 on the bottom side of the protective cover set 150.

Figure 10:
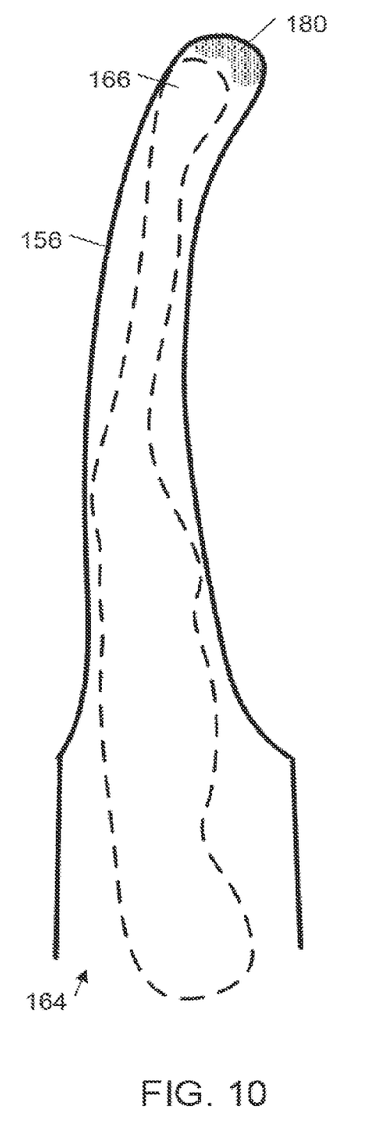
FIG. 10 is diagrammatic perspective view of a medical probe inserted within the probe cover shown in FIG. 9B.

Referring to FIGS. 9A and 10, in some embodiments of the protective cover set 150, a gel 180 is placed in the distal end of the probe cover 156 either before, during, or after the sealed joint 162 between the outer wrapper layers 152, 154 and the probe cover is formed. In some embodiments, the gel 180 may be, for example, an ultrasound transmission gel. In the illustrated embodiment, the probe cover 156 with the narrowed opening 164 covers the medical probe 166 to protect it from contamination.

The details of specific implementations described herein may be specific to particular embodiments of particular inventions and should not be construed as limitations on the scope of any claimed invention. For example, features that are described in connection with separate embodiments may also be incorporated into a single embodiment, and features that are described in connection with a single embodiment may also be implemented in multiple separate embodiments.

In addition, the disclosure of steps, tasks, operations, or processes being performed in a particular order does not necessarily require that those steps, tasks, operations, or processes be performed in the particular order; instead, in some cases, one or more of the disclosed steps, tasks, operations, and processes may be performed in a different order or in accordance with a multi-tasking schedule or in parallel.

Other embodiments are within the scope of the claims.

The invention claimed is:

1. A protective cover for a medical probe, comprising:
    a probe cover having a three-dimensional shape configured to receive a working end of a medical probe inserted in use into an open proximal end portion of the probe cover; and
    an outer wrapper comprising two outer protective layers, one on each side of the probe cover,
    wherein the outer protective layers and the proximal end portion of the probe cover are bonded together along a joint at the proximal end portion of the probe cover, and
    wherein a remaining portion of the probe cover beyond the proximal end portion is unattached to the outer wrapper, and a remaining portion of the outer protective layers are bonded together along an extension of the joint at the proximal end portion of the probe cover.

2. The protective cover of claim 1, wherein a distal portion of the probe cover is inverted.

3. The protective cover of claim 1 further comprising a tack joint between an outer protective layer and the probe cover at the proximal end portion of the probe cover.

4. The protective cover of claim 1, wherein a distal portion of the probe cover is folded.

5. The protective cover of claim 4 further comprising a gel located in the folded distal portion of the probe cover.

6. The protective cover of claim 1 wherein two sides of the probe cover are bonded to each other along the joint at the proximal end portion of the probe cover.

7. The protective cover of claim 6 wherein a bond strength between the two sides of the probe cover is greater than a bond strength between the outer protective layers and the probe cover.

8. The protective cover of claim 1 wherein the outer wrapper is made of a thermoplastic polymer material that is different from a thermoplastic polymer material from which the probe cover is made.

* * * * *